United States Patent [19]

Perry

[11] 3,942,941
[45] Mar. 9, 1976

[54] ARRANGEMENT FOR STERILIZING A STREAM OF GAS

[75] Inventor: John H. Perry, Doraville, Ga.

[73] Assignee: The Mead Corporation, Dayton, Ohio

[22] Filed: Nov. 1, 1974

[21] Appl. No.: 519,997

Related U.S. Application Data

[63] Continuation of Ser. No. 409,986, Oct. 26, 1973, abandoned.

[52] U.S. Cl. .......................... 432/29; 21/91; 21/92; 432/2
[51] Int. Cl.² .................................... A61L 3/00
[58] Field of Search ............... 21/2, 71, 91, 92, 110; 432/219–221, 54, 29, 2

[56] References Cited
UNITED STATES PATENTS

| 958,259 | 5/1910 | LeFaguays | 21/92 |
| 1,311,235 | 7/1919 | Kemp et al. | 432/29 |
| 3,291,563 | 12/1966 | Martin | 21/91 |
| 3,513,627 | 5/1970 | Doucette et al. | 21/91 |
| 3,549,312 | 12/1970 | Ernst | 21/91 |
| 3,549,528 | 12/1970 | Armstrong | 21/91 |
| 3,598,517 | 8/1971 | Beecher | 21/91 |
| 3,606,282 | 9/1971 | Stookey | 432/29 |
| 3,689,039 | 9/1972 | Kilgren | 432/29 |

*Primary Examiner*—John J. Camby
*Assistant Examiner*—Henry C. Yuen
*Attorney, Agent, or Firm*—Walter M. Rodgers

[57] ABSTRACT

A source of gas under pressure is interconnected by conduit means with at least one point of use through gas conditioning means which may include filter means and heater means and retention means specially arranged to maintain the temperature of a stream of gas for a desired period of time and a source of sterilizing fluid is interconnected with the conduit means and is arranged to scavenge the conduit means, the point of use and the gas conditioning means in coordination with the opening of vent means associated with the point of use, the gas conditioning means and the conduit means.

2 Claims, 1 Drawing Figure

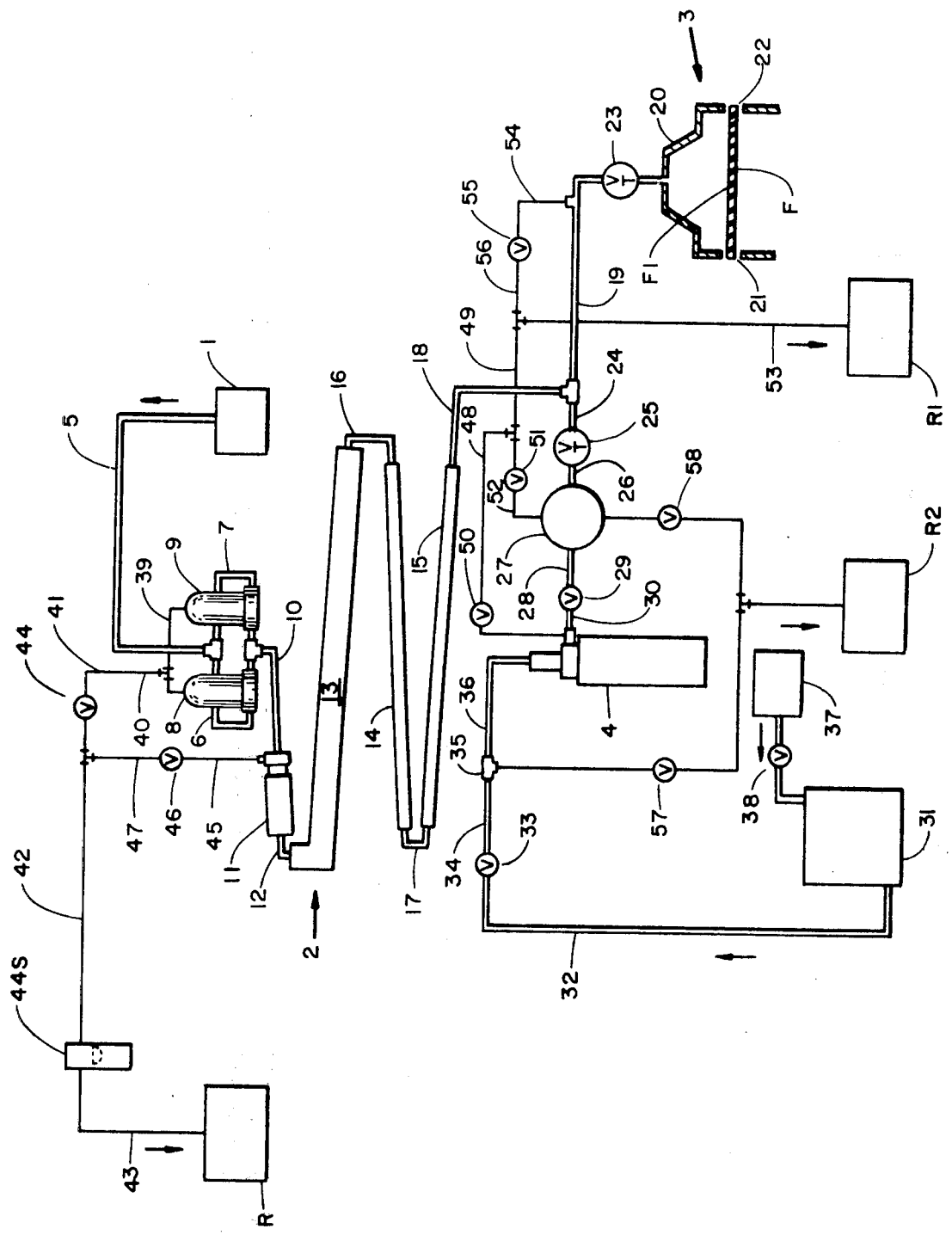

ARRANGEMENT FOR STERILIZING A STREAM OF GAS

This is a continuation of application Ser. No. 409,986 filed Oct. 26, 1973, now abandoned.

Certain processes and machines which are used in conjunction with substances which are subject to virus and bacteriological contamination must utilize sterilized components and must operate in regions of sterile atmosphere or of pressurized gas. One example of such a process and machine is the so-called form-fill-seal machine one form of which is disclosed and claimed in U.S. patent application Ser. No. 238,872 filed Mar. 28, 1972 now U.S. Pat. No. 3,750,367 issued Aug. 7, 1973. While this invention is not limited to use with a machine of the form-fill-seal type, it is well suited for application to such a machine and is concerned primarily with sterilizing a stream of gas by heating the gas to a desired temperature and by maintaining the flowing gas at a temperature which is sufficiently high and for an adequate period of time to sterilize the gas while it is flowing to a point of use.

According to the invention in one form, a stream of gas is directed through heater means and its temperature elevated to a desired level and thence through suitable retention means which is specially constructed to maintain the stream of gas at a desired temperature level for a sufficient period of time to effect sterilization of the stream of gas.

For a better understanding of the invention reference may be had to the following detailed description taken in conjunction with the accompanying single drawing FIGURE which takes the form of a schematic representation of a system constructed according to one form of the invention.

In the drawing gas under pressure is supplied from source 1 through gas conditioning means generally designated by the numeral 2 to points of use designated by the nummerals 3 and 4. Source 1 may constitute a compressor which is supplied from atmosphere with atmospheric air and which supplies compressed gas to the system through conduit 5 which in turn is connected through branch conduits 6 and 7 with a pair of parallel connected filters 8 and 9 constructed to remove a substantial portion of foreign substances from the gas supplied to the filters through conduit 5. Preferably filters 8 and 9 are of the micropore type having an efficiency of 99.99 percent for particles larger than 0.6 micron. Gas from filters 8 and 9 is supplied through conduit 10 to heater element 11 the output of which is supplied by conduit 12 to retention chamber 13 connected in series with cooling devices 14 and 15 via a conduit 16. Cooling elements 14 and 15 are connected in series by conduit 17. Gas is supplied from cooling device 15 through conduit 18 and conduit 19 to the point of use 3. In practice point of use 3 in one application of the invention constitutes a hood shown in section and indicated by the numeral 20 and provided with slits 21 and 22 which receive opposite edges of a strip of film F. Thus the interior of hood 20 is filled with sterile gas and the upper surface such as F1 is bathed in a sterile atmosphere. In one application of the invention the pressure within hood 20 is approximately 2/10 of an inch of water and is simply sufficient to cause slight leakage to atmosphere from the interior of the tunnel and by this means to preclude the possibility that contaminated atmospheric air may enter the interior of tunnel 20. The low pressure within the tunnel 20 is regulated by manually operable throttle valve 23.

Simultaneously with the application of low pressure gas to the interior of tunnel 20, substantially high pressure is supplied from conduit 18 to the forming press schematically represented by the numeral 4. Such gas passes through conduit 24 manually operable throttle valve 25, conduit 26, surge tank 27, conduit 28, electrically controlled valve 29, short conduit 30 to the forming press 4. Of course the adjustment of throttle valve 25 accommodates the application of pressure to the forming press which may be of the order of magnitude of six or seven bars.

Where the sterile system of this invention is used in conjunction with a form-fill-seal machine, the relatively high pressure supplied to forming press 4 serves to aid in forming units such as containers which are formed from film such as F which is supplied in such a machine through tunnel 3 from the forming press 4.

Heating chamber 11 is operated at elevated temperatures with the purpose of destroying bacteriological or virus elements which may succeed in passing through the filters 8 and 9. To this end, the discharge of gas from heater 11 at approximately 800°F. is supplied through conduit 12 to retention chamber 13 and simply is retained in chamber 13 for an appreciable period of time due to the substantial volume of retention chamber 13 compared to the size of conduit 12 and the rate of flow of gas therethrough. Thus adequate kill time is afforded by the retention chamber 13 which prolongs the elevated temperature supplied by heater device 11 for a substantial period of time such that all bacteriological and virus contamination is completely destroyed.

Heater chamber 10 elevates the temperature of a flowing stream of gas which flows around a serpentine heater element mounted on a threaded ceramic core and housed in a suitable quartz or aluminum oxide housing.

In order to destroy all viral and bacterial infestation in a gas, the gas must be maintained at a sufficiently high level of temperature for a sufficiently long time. Of course the higher the temperature of gas, the shorter the time required to effect complete extermination of all infestation. The following is a tabulation of gas temperatures correlated with extermination time:

| Gas Temperature | Extermination Time |
| --- | --- |
| 300°C | 6 seconds |
| 364°C | .6 seconds |
| 426°C | .06 seconds |

From the above tabulation, it is apparent that for each incremental increase of approximately 62° to 64° centigrade in temperature of the gas in the range of temperature stated, the extermintion time is decreased 90 percent to 10 percent.

The volume of gas required at the point of use or at the points of use per unit of time is known based on the requirements of the system. With the required rate of flow of gas as a starting point, the heater means is simply chosen so as to accommodate the required rate of flow and so as to elevate the temperature to a desired level determined by the above compilation such for example as 426° centigrade. The retention time then must be a minimum of 0.06 seconds according to the above tabulation.

Thus in accordance with a principal facet of this invention, the temperature of gas is maintained at a level in excess of the required minimum by the use of a retention chamber constructed so that its cross sectional area in a plane normal to the direction of flow therethrough from the heater means is greater than the corresponding dimension of the heater means and of the conduit interconnecting the heater means and the retention means such that the volume flowing through the insulated retention chamber per unit of time is increased and the linear rate of flow per unit volume is decreased directly according to the increase in cross sectional area of the retention chamber in a plane normal to the direction of flow of gas therethrough. By this means the time of retention within the retention chamber of a unit volume of gas is correspondingly and directly increased for a predetermined minimum length of the retention chamber in the direction of flow of gas therethrough. As a matter of practice it ordinarily is desirable to allow a margin of safety and to construct the retention chamber of a length which greatly increases the extermination time so as to make certain that adequate sterilization is effected.

While this invention is not limited to a particular retention chamber or rate of flow of gas therethrough, one practical arrangement utilizes a cylindrical retention chamber having an inside diameter of two and one quarter inches and a length of nine feet and the rate of flow through the retention chamber is approximately 60 standard cubic feet per minute.

The gas supplied by retention chamber 13 through conduit 16 through cooling jackets 14 and 15 is reduced substantially in temperature to usable levels. For example the temperature of gas in conduit 18 before being supplied to the tunnel 20 or to the forming press 4 could be approximately 100°F. Of course the temperature is not critical at this stage and may be regulated as desired for particular applications of the invention as is obvious.

Surge tank 27 is simply an enclosure under pressure and serves as a buffer to insure that adequate volume and pressure of gas is always available for application in the relatively high pressure point of use identified in the drawings by the numeral 4 and which may take the form of a forming press if the invention is used in conjunction with a form-fill-seal machine.

From the above description it is apparent that sterile atmosphere is provided through which the film F is applied to the forming press and that relatively high pressure gas used in the forming operation is sterile and hence non-contaminating so that the containers formed by the forming press may be immediately filled with substances which are subject to contamination and when so filled and promptly sealed under sterile conditions such substances may be retained for long periods of time without refrigeration and such a result constitutes one of the advantages achieved and made possible pursuant to this invention.

Of course it would be futile to insure that sterilized gas is prepared by the filter elements 8 and 9 and by heater chamber 11 in conjunction with the retention chamber 13 if the interior surfaces of those elements as well as of the various conduits and the points of use were contaminated. Thus it is necessary to sterilize all interior surfaces prior to operating the system as a whole.

For the purpose of sterilizing the system before use, a sterilizing tank generally designated by the numeral 31 is employed and is interconnected by conduit 32, control valve 33, conduit 34, T connection 35 and conduit 36 with the forming press 4.

It is within the purview of this invention to utilize any suitable sterilizing fluid. One suitable sterilizing fluid is hydrogen peroxide of proper concentration and temperature and means for forcing hydrogen peroxide in liquid form through the system may constitute a source of compressed air schematically designated in the drawing by the numeral 37. Such air under pressure may be supplied through electromagnetically controlled valve 38 to the tank 31. Thus with pressure applied to tank 31 and with the valving of the system properly adjusted, sterilizing fluid may be supplied to the various components and retained therein for a time sufficient completely to sterilize all interior surfaces which come in contact with the gas supplied to the system from source 1.

Of course the system is substantially fluid tight with the exception of the leakage above described in conjunction with tunnel 20 so that in order to scavenge the system thoroughly and completely with sterilizing fluid such as liquid from tank 31, suitable vent means must be provided and must be controlled in an appropriate manner. For example the filters 8 and 9 are interconnected through vent lines schematically shown at 39, 40, 41, 42 and 43. These vent lines are controlled by vent valve 44 which is normally closed and which is opened prior to the application of pressure to tank 31 by opening valve 38. Interconnected between conduits 42 and 43 is a sensing device 44S which in practice may constitute a float switch by which the presence of sterilizing liquid is sensed and by which a determination may be made to the effect that filters 8 and 9 are completely filled with sterilizing liquid. Heating chamber 11 is interconnected by vent conduit 45, vent control valve 46 and conduit 47 with conduit 42 so that when vent valve 46 is opened sterilizing liquid may completely fill the interior of heating chamber 11, retention chamber 13, water jackets 14 and 15 and their associated conduits which are all connected in series. Valves 57 and 58 are normally closed drain valves.

For the purpose of venting the points of use 3 and 4 and the conduits associated therewith, schematically designated vent conduit 48 is connected with forming press 4 and with conduit 49, vent valves 50 and 51 and conduit 53 to atmosphere. Tunnel 20 and its associated conduit 19 and valve 23 are vented through vent line 54, vent valve 55, conduit 56 and conduit 53.

From the above description it is apparent that a venting operation is initiated by simultaneously opening vent valves 44, 46, 50, 51, 55 and control valves 33 and 38. Under these conditions, pressure from source 37 is applied to the interior of tank 31 and such pressure forces sterilizing liquid through conduit 32, control valve 33, conduit 34, T connection 35, conduit 36, point of use 4, conduits 30, valve 29, surge tank 27, conduit 26, valve 25, conduit 24, conduit 19 to point of use 3. Simultaneously sterilizing liquid is supplied through conduits 18, through water jackets 14 and 15 and their associated conduits 17 and 16, retention chamber 13, conduit 12, heater 11, conduit 10 and through the filters 8 and 9. Ultimately the sterilizing liquid passes through the vent valves 44 and 46 and their associated conduits and through conduit 42, sensing device 44S and outwardly through conduit 43 to a suitable receptacle designated by the letter R. The presence of liquid in sensing device 44S constitutes a clear indication that the components of the system including all conduits are thoroughly scavenged of gas and the interior surfaces are thus in contact with sterilizing liquid. Following the scavenging operation vent valves 44, 46, 50, 51, 55 are closed. The system is maintained under this condition for a suitable length of time such as 30 to 40 minutes. Following which time the system is thoroughly sterilized and it is then simply necessary to drain the liquid from the system and toward this end drain valves 57 and 58 which are closed during a sterilizing procedure are opened so that the liquid may drain away to a suitable receptacle R2. Obviously from the drawing, drain valve 57 serves to drain conduits 34 and 36 as well as T-connection 35, control valve 33 and conduit 32. Drain valve 58 serves to drain the surge tank, conduits 28, 30, valve 29, conduit 26, points of use 3 and 4 and cooling devices 14, 15, retention chamber 13, heater element 12, filters 8 and 9 and the conduits associated therewith. Following the drainage of the system, control valve 33 is closed so as to prevent the application of pressure gas to the tank 31. Of course the application of heated sterilized gas supplied from filters 8 and 9 and heaters 11 serves further to scavenge those elements of any residual sterilizing liquid.

From the above description it is apparent that a completely sterile system is provided which supplies a low pressure sterile gas to a point of use such as tunnel 20 and a high pressure gas to a point of use such as forming press 4 and that means are also provided for pre-sterilizing all components prior to operating the system.

The embodiments of the invention in which an exclusive property or privilege is claimed are defined as follows:

1. A method of sterilizing a stream of gas flowing under pressure through heater means, retention means, and cooling means interconnected via conduit means with each other and with a point of use, the method comprising heating said stream of gas to a temperature of approximately 300°C. in said heater means, maintaining said gas at approximately 300°C. for approximately 6 seconds in said retention means, cooling said gas substantially via said cooling means and supplying the sterilized and cooled gas to a point of use under pressure.

2. A method according to claim 1 wherein said stream of gas is heated to a temperature in excess of 300°C and wherein the temperature of said gas is maintained at a level in excess of 300°C. for a time less than six seconds, the reduction in time being of the order of 90 percent for each increment of a temperature of approximately 63°C. above 300°C.

* * * * *